(12) United States Patent
Carton et al.

(10) Patent No.: US 10,512,439 B2
(45) Date of Patent: Dec. 24, 2019

(54) METHOD OF CONTRAST ENHANCED BREAST IMAGING, AND CONTRAST AGENT REFERENCE INSERT

(71) Applicant: GENERAL ELECTRIC COMPANY, Schenectady, NY (US)

(72) Inventors: Ann-Katherine Carton, Buc (FR); Sylvie Puong, Buc (FR); Razvan Gabriel Iordache, Buc (FR); Serge Muller, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 269 days.

(21) Appl. No.: 14/901,890

(22) PCT Filed: Jul. 3, 2013

(86) PCT No.: PCT/IB2013/001765
§ 371 (c)(1),
(2) Date: Dec. 29, 2015

(87) PCT Pub. No.: WO2015/001372
PCT Pub. Date: Jan. 8, 2015

(65) Prior Publication Data
US 2016/0128659 A1    May 12, 2016

(51) Int. Cl.
*A61B 6/00* (2006.01)
(52) U.S. Cl.
CPC .............. *A61B 6/481* (2013.01); *A61B 6/502* (2013.01); *A61B 6/583* (2013.01)

(58) Field of Classification Search
CPC .......... A61B 6/481; A61B 6/502; A61B 6/583
See application file for complete search history.

(56) References Cited

U.S. PATENT DOCUMENTS

| 3,578,971 | A | * | 5/1971 | Lasky | .................... A61B 6/502 378/180 |
| 4,649,561 | A | * | 3/1987 | Arnold | ................. G09B 23/286 250/252.1 |
| 4,759,045 | A | * | 7/1988 | Lasky | .................... A61B 6/502 378/162 |
| 5,335,260 | A | | 8/1994 | Arnold | |

(Continued)

FOREIGN PATENT DOCUMENTS

FR    2873835 A1    2/2006
JP    S59-105442 A    6/1984

(Continued)

OTHER PUBLICATIONS

Unofficial English translation of Japanese Search Report issued in connection with corresponding JP Application No. 2016-522879 dated Jan. 23, 2017.

(Continued)

*Primary Examiner* — Amelie R Gillman
(74) *Attorney, Agent, or Firm* — Fletcher Yoder, P.C.

(57) ABSTRACT

A method of contrast enhanced breast imaging, comprising injecting a contrast agent in a breast of a patient, imaging at the same time both said breast and a reference insert containing at least one known concentration of said contrast agent, quantifying enhancement of contrast enhanced breast image by comparing said breast image and reference insert image.

8 Claims, 2 Drawing Sheets

(56) References Cited

U.S. PATENT DOCUMENTS

| | | | |
|---|---|---|---|
| 6,272,200 B1* | 8/2001 | Pan | G06T 11/005 378/15 |
| 6,904,123 B2 | 6/2005 | Lang | |
| 2002/0067798 A1 | 6/2002 | Lang | |
| 2002/0186818 A1 | 12/2002 | Arnaud et al. | |
| 2003/0063704 A1* | 4/2003 | Lang | A61B 6/505 378/54 |
| 2003/0122544 A1* | 7/2003 | Parker | A61B 8/587 324/309 |
| 2005/0031180 A1 | 2/2005 | Jeunehomme et al. | |
| 2006/0025680 A1 | 2/2006 | JeuneHomme et al. | |
| 2007/0242794 A1* | 10/2007 | Stanton | A61B 6/02 378/5 |
| 2008/0167552 A1 | 7/2008 | Bouchevreau et al. | |
| 2008/0253503 A1 | 10/2008 | Proksa | |
| 2009/0028405 A1* | 1/2009 | Degani | A61B 6/481 382/131 |
| 2009/0076382 A1* | 3/2009 | Shepherd | A61B 6/12 600/426 |
| 2010/0054401 A1* | 3/2010 | Blendl | A61B 6/4233 378/37 |
| 2010/0140500 A1* | 6/2010 | Jesseph | A61N 5/10 250/454.11 |
| 2010/0266190 A1 | 10/2010 | Zagorchev et al. | |
| 2012/0027167 A1* | 2/2012 | O'Brien | A61B 6/032 378/20 |
| 2012/0049584 A1 | 3/2012 | Manders et al. | |
| 2012/0189551 A1 | 7/2012 | Frank et al. | |
| 2013/0200900 A1 | 8/2013 | Buurman et al. | |
| 2014/0369582 A1* | 12/2014 | Partain | G06T 7/0014 382/131 |

FOREIGN PATENT DOCUMENTS

| | | |
|---|---|---|
| JP | H10-323345 A | 12/1998 |
| JP | 2004507309 A | 3/2004 |
| JP | 2004-243128 A | 9/2004 |
| JP | 2004248297 A | 9/2004 |
| JP | 2004254918 A | 9/2004 |
| JP | 2008161690 A | 7/2008 |
| JP | 2009508616 A | 3/2009 |
| JP | 2009-522055 A | 6/2009 |
| JP | 2013539705 A | 10/2013 |
| JP | 2014504603 A | 2/2014 |
| WO | 2007/126572 A2 | 11/2007 |
| WO | 2012040611 A1 | 3/2012 |
| WO | 2012049584 A1 | 4/2012 |
| WO | 2012122399 A1 | 9/2012 |

OTHER PUBLICATIONS

Machine translation and Notification of Reasons for Refusal issued in connection with corresponding JP pplication No. 2016-522879 dated Aug. 8, 2017.

M. Skarpathiotakis et al., "Development of contrast digital mammography", Med. Phys. 29, 2419, 2002.

Jong et al., "Contrast-enhanced Digital mammography: Initial Clinical Experience", Radiology, vol. 228, pp. 842-850, 2003.

JP Office Action dated Feb. 7, 2017 issued in corresponding JP Application No. 2016522879.

International Search Report and Written Opinon dated Dec. 20, 2013 which was issued in connection with PCT Patent Application No. IB2013/001765 which was filed on Jul. 3, 2013.

* cited by examiner

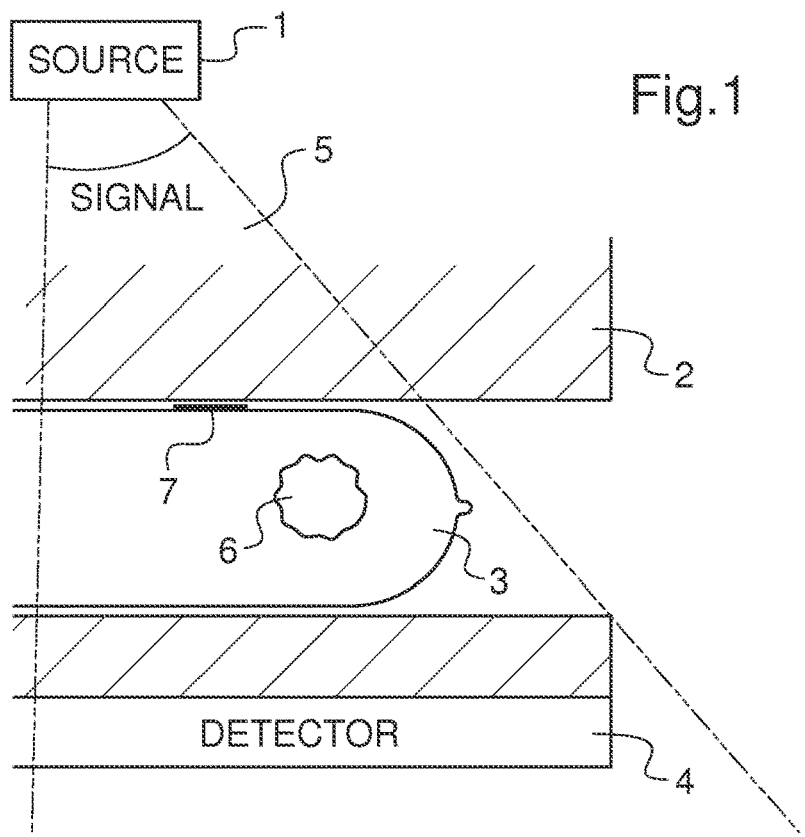
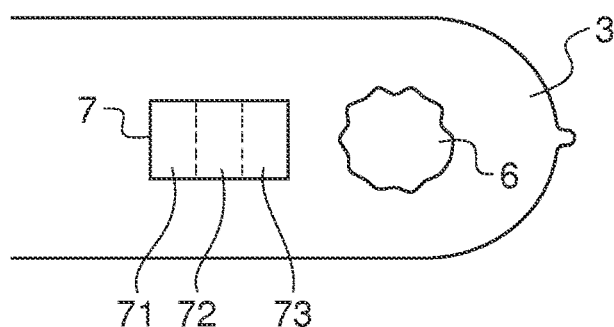
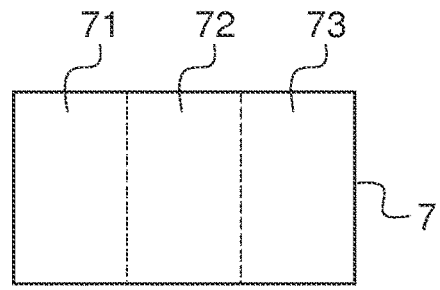

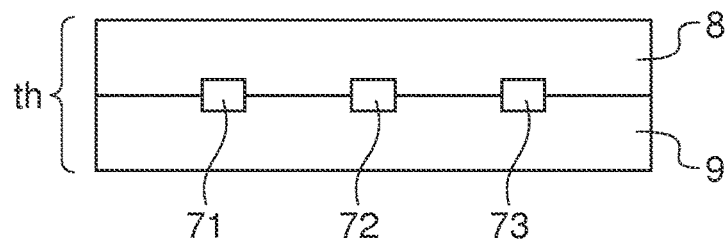
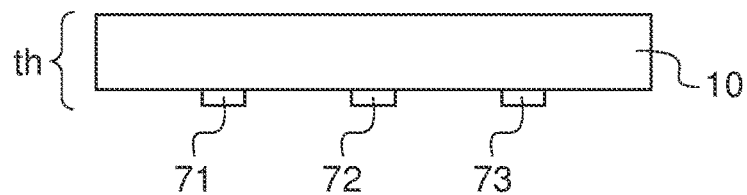
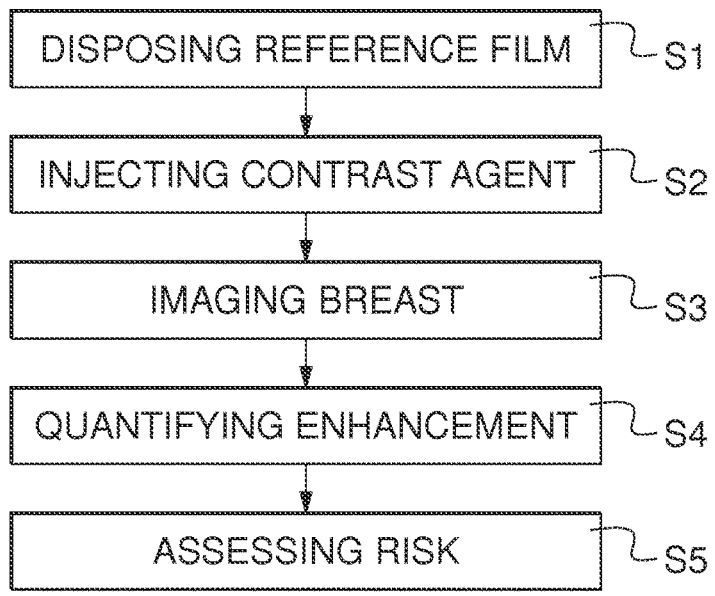
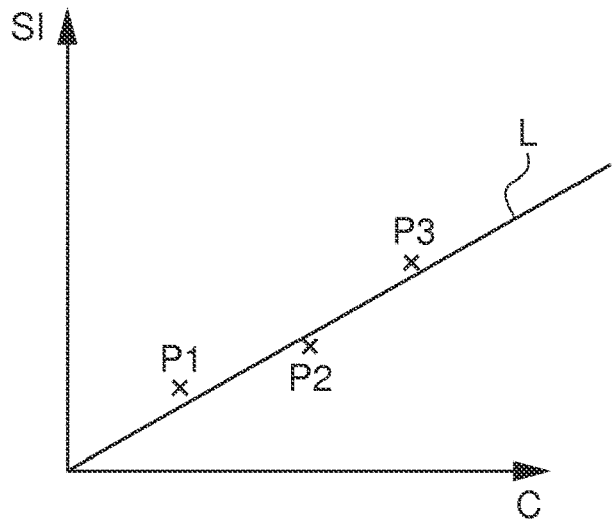

METHOD OF CONTRAST ENHANCED BREAST IMAGING, AND CONTRAST AGENT REFERENCE INSERT

FIELD OF THE INVENTION

Embodiments of the present invention relate to methods of contrast enhanced breast imaging and to contrast agent reference inserts.

BACKGROUND OF THE INVENTION

Contrast enhanced breast imaging techniques are able to provide functional information of breast lesions by using an intravenous contrast agent, usually iodine. Today, clinical diagnosis of contrast enhanced x-ray imaging images is often based on the qualitative assessment of contrast agent uptake and characterization of the morphology of the enhancing lesions.

According to a first prior art, which concerns classical contrast enhanced spectral mammography, it is known to inject a contrast agent which will propagate in the breast of a patient, to image the breast, to assess qualitatively enhancement of the contrast enhanced breast image to detect whether there is or not an identified risk of a breast lesion, for example of a breast cancer. A limitation of this first prior art is that it allows only for a qualitative assessment of the enhancement of the contrast enhanced breast image. In some cases, this qualitative assessment may lead to insufficiently precise risk assessment or even to erroneous diagnostic of the lesion risk of the patient breast.

According to a second prior art, for example described in "Jong et al. Contrast-enhanced Digital Mammography: Initial Clinical Experience, Radiology 2003", it is known a phantom image made with a contrast agent insert and used as a reference to try and quantify another contrast enhanced breast image performed later on. A drawback of this second prior art lies in the fact that a phantom image cannot reproduce accurately all the clinical imaging conditions, among which specific breast thickness, specific breast area covering the detector of the imaging system, specific glandularity of the breast, specific effective spectrum and scatter conditions. Failing to reproduce accurately those clinical imaging conditions can lead to imprecise or even to inaccurate quantification of the enhancement of the contrast enhanced breast image.

According to a third prior art, for example described in U.S. Pat. No. 5,335,260, it is known a bone density quantification method using a reference imaged simultaneously with the body of a patient. Such third prior art does not use any contrast agent injection nor does it concern breast imaging.

According to embodiments of the invention, it is noticed that none of those prior art documents allows for an accurate and precise quantification of the enhancement of the contrast enhanced breast image to more accurately evaluate breast lesion risk and or to more accurately follow up an identified breast lesion.

SUMMARY OF THE INVENTION

The object of embodiments of the present invention is to alleviate at least partly the above mentioned drawbacks.

More particularly, embodiments of the invention provide for a contrast enhanced breast imaging method which will allow for a more precise quantification of the enhancement of the contrast enhanced breast image, by imaging at the same time, and not at different time points, the breast and a reference insert containing at least one known concentration of contrast agent. Therefore, the clinical imaging conditions being the same or very similar for both the reference insert and the breast, and the quantification will be more precise and more accurate.

In an embodiment, the reference insert is a film, which being thin, will cause only minimal distortion to the contrast enhanced breast image. Therefore, the perturbations introduced by the reference film being minimized, the quantification then obtained by using this reference film, will be all the more accurate and all the more precise.

This object is achieved with a method of contrast enhanced breast imaging, comprising: injecting a contrast agent in a breast of a patient, imaging at the same time both the breast and a reference insert containing at least one known concentration of the contrast agent, quantifying enhancement of contrast enhanced breast image by comparing the breast image and reference insert image. In an embodiment, the breast and reference insert are imaged simultaneously, and then breast image and reference insert image are indeed two portions of a global image encompassing both breast and reference insert.

Another object is also achieved with an insert, containing at least one known concentration of a contrast agent, so as to serve as a comparative reference for a contrast enhanced breast image to quantify enhancement of the contrast enhanced breast image, wherein the insert is a film. The structure of this reference insert is so interesting by itself that it can be used not only for contrast enhanced breast imaging but also for example for calibration of contrast enhanced breast imaging system or for quality control of contrast enhanced breast imaging system.

Still another object is also achieved with a film containing at least one known concentration of a contrast agent used in contrast enhanced breast imaging. The structure of this reference insert is so interesting by itself that it can be used not only for contrast enhanced breast imaging but also for example for calibration of contrast enhanced breast imaging system or for quality control of contrast enhanced breast imaging system. A phantom with both breast tissue equivalent and iodine structures to assess and monitor image quality of contrast enhanced spectral mammography is provided in an embodiment. More particularly, this phantom comprises all together several different known concentrations of contrast agent and two different breast tissue equivalent textures, glandular and adipose.

For breast cancer diagnosis, quantification of contrast agent enhancement can be useful to assist in differential diagnosis. Quantification of contrast agent enhancement can also result in an improved monitoring of the therapeutic response for cancer patients that would have a contrast enhanced breast imaging exam every few months.

Image quality metrics, like average signal intensity, signal to noise ratio, signal difference to noise ratio, can be computed in different areas of the phantom, for example with or without iodine, and used to assess and/or monitor image quality consistency.

Visual scoring can be implemented too. For example, one can superpose the film on a PMMA (poly (methyl methacrylate)) film phantom and do a contrast detail analysis on the iodine inserts in the recombined image. This can be used either for performance evaluation, for instance what is the smallest visible insert size for a given concentration, or for quality control, in a way similar to ACR (American College of Radiology) accreditation phantom scoring.

Embodiments may comprise one or more of the following features, which can be taken separately or together, either in partial combination or in full combination.

In an embodiment, the contrast agent is iodine.

In another embodiment, the reference insert is a film. Using a film having a relatively low thickness presents the advantage of distorting only minimally the contrast enhanced breast image. Distortion of scatter and beam hardening in the breast are minimized. No or little image artifacts are introduced in this contrast enhanced breast image, on the contrary to using an iodine insert which non negligible thickness would introduce such image artifacts. In an embodiment, the film has a thickness which is less than 2 mm, particularly less than 1 mm, more particularly less than 0.5 mm.

In an embodiment, the film is multilayered with contrast agent encapsulated in between layers. The contrast agent can that way be precisely dosed in each area corresponding to a specific known concentration of contrast agent. The contrast agent being well protected, the precisely defined concentrations of contrast agent in different areas of the film can be kept stable over time.

In another embodiment, the contrast agent is printed on the film or printed in the film. This way, manufacturing of the film will allow for a film very thin, all the better with respect to little or minimized breast image distortion.

In an embodiment, the reference insert contains several different known concentrations of the contrast agent respectively disposed on different areas of the reference insert, particularly 2 to 5 different known concentrations of the contrast agent, more particularly 3 different known concentrations of the contrast agent. These several reference values will allow for a more precise calibration, leading then to a more precise quantification of the enhancement of the contrast enhanced breast image.

In an embodiment, the lowest concentration of the different known concentrations of the contrast agent is less than 2 mg iodine per centimeter square for the thickness of the reference insert, more particularly less than 1 mg iodine per centimeter square for the thickness of the reference insert. In an embodiment, the highest concentration of the different known concentrations of the contrast agent is more than 5 mg iodine per centimeter square for the thickness of the reference insert. With such minimal and maximal values of the contrast agent concentration range, the reference values will allow for a more precise calibration, leading then to a more precise quantification of the enhancement of the contrast enhanced breast image.

In an embodiment, the reference insert is disposed on imaged breast surface, beside a formerly identified breast lesion. That way, the reference insert image and the damaged breast region being close to each other, their conditions will be very similar, allowing then for an easier and more accurate comparison between both images, leading to a more efficient and more precise quantification of the enhancement of the contrast enhanced breast image.

In an embodiment, there are signal intensities corresponding to the known concentrations of the contrast agent or signal intensity differences between signal intensities corresponding to the known concentrations of the contrast agent and signal intensity corresponding to breast background are plotted versus the known reference concentrations to assess a fitting function which will be used to quantify the enhancement of the contrast enhanced breast image. This fitting function assessment allows to map signal intensity levels into iodine concentration levels.

In an embodiment, the fitting function is linear. Hence, the comparison between reference insert image and breast image will lead to accurate and simple quantification of enhancement of contrast enhanced breast image.

In an embodiment, the method is performed at different times to follow up a breast cancer therapy. Indeed, the quantification, and especially a precise quantification, is then all the more important that the differences from one contrast enhanced breast image to a later contrast enhanced breast image may be tiny; in this later case, a qualitative assessment of differences of enhancement from one contrast enhanced breast image to the next one can become quite delicate.

In an embodiment, the method is an x-ray contrast enhanced spectral mammography, more particularly a dual energy contrast enhanced spectral mammography. Instead of dual energy contrast enhanced spectral mammography, temporal contrast enhanced spectral mammography can be used too. Contrast enhanced spectral mammography already exists in the art, but the proposed contrast enhanced breast imaging method will allow for a quantification until now unknown, since in the art the assessment of enhancement is only qualitative. The breast and the reference insert may be imaged simultaneously.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 1 shows an example of a setup allowing for performing the contrast enhanced breast imaging method according to an embodiment of the invention.

FIG. 2 shows an example of a disposition of a reference film on a patient breast during performing the contrast enhanced breast imaging method according to an embodiment of the invention.

FIG. 3 shows a top view of an example of a reference film used by the contrast enhanced breast imaging method according to an embodiment of the invention.

FIG. 4 shows a side view of an example of a first embodiment of a reference film used by the contrast enhanced breast imaging method according to an embodiment of the invention.

FIG. 5 shows a side view of an example of a second embodiment of a reference film used by the contrast enhanced breast imaging method according to an embodiment of the invention.

FIG. 6 shows an example performing the contrast enhanced breast imaging method according to an embodiment of the invention.

FIG. 7 shows an example of a linear fitting function used when performing the contrast enhanced breast imaging method according to an embodiment of the invention.

DETAILED DESCRIPTION OF THE INVENTION

FIG. 1 shows an example of a setup allowing for performing the contrast enhanced breast imaging method according to an embodiment of the invention. The system comprises an x-ray source 1, an x-ray detector 4, and a compression paddle 2. A patient breast 3 is introduced and compressed within the compression paddle 2. Source 1 emits a cone of x-ray signal 5 to image breast 3 on surface of detector 4. Breast 3 contains a lesion 6 that has for example been identified in a previous clinical exam and for which there is a therapy on going. Here, this new exam is then a follow up of this therapy. The position of the lesion 6 in the breast 3 is roughly known. Therefore, it is possible to dispose the reference film 7 close to the lesion 6, so that the reference film 7 and lesion 6, which are imaged at the same time, here simultaneously in the very same image, can be imaged in same or very similar conditions.

FIG. 2 shows an example of a disposition of a reference film on a patient breast during performing the contrast enhanced breast imaging method according to an embodiment of the invention. To perform the contrast enhanced breast imaging, a reference film 7 has been disposed on the breast 3, close to the identified lesion 6 or close to another zone of specific interest in the breast 3. This reference film 7 contains a contrast agent, for example iodine. This reference film 7 presents several zones, here 3 zones 71, 72 and 73, respectively comprising different known concentrations of the contrast agent. Zones 71 to 73 may comprise respectively a low concentration zone 71, for example about 1 mg iodine per centimeter square for the given thickness of the zone 71, a medium concentration zone 72, for example about 4 mg iodine per centimeter square for the given thickness of the zone 72, a high concentration zone 73, for example about 6 mg iodine per centimeter square for the given thickness of the zone 73. The zones 71 to 73 being close to the lesion 6, imaging conditions, including the type (either glandular or adipose) and the thickness, of breast structure which the emitting radiation will have to go through, will be very similar, if not practically identical. The reference film 7 may only touch the breast 3 without being fixed on it, the reference film 7 then only has to be maintained between breast 3 and compression paddle 2. The reference film 7 may also be temporarily attached to the breast 3, for the duration of the imaging. As an alternative, the reference film 7 may also be attached on the paddle 2 or on the patient support plate.

FIG. 3 shows a top view of an example of a reference film used by the contrast enhanced breast imaging method according to an embodiment of the invention. The reference film 7 comprises here three different zones 71, 72 and 73, comprising agent contrast with respectively three different known concentrations. There could be more or less such zones in the reference film 7, more particularly between 2 and 5 such zones. The reference film 7 presents a rectangular form. But its form could be different; it could be for example square, or round or oval. There could be different repartitions of the concentration zones on the reference film 7, either mono-dimensional like on FIG. 3 or bi-dimensional repartition.

FIG. 4 shows a side view of an example of a first embodiment of a reference film used by the contrast enhanced breast imaging method according to an embodiment of the invention. The reference film 7 is a multilayered structure. There are a top layer 8 and a bottom layer 9. Capsules of liquid contrast agent are sandwiched in between layers 8 and 9. These capsules constitute the zones 71 to 73. The reference film 7 is rather thin. The global thickness th of the reference film 7 is kept quite low, no more than 1 or 2 mm.

FIG. 5 shows a side view of an example of a second embodiment of a reference film used by the contrast enhanced breast imaging method according to an embodiment of the invention. The reference film 7 is a monolayered structure. There is only one layer 10. Zones 71 to 73 are printed on layer 10. Zones 71 to 73 are solid marks that are fixed on the surface of layer 10. The reference film 7 is really thin and thinner than the reference film of FIG. 4. The global thickness th of the reference film 7 is kept low, less than 1 mm, maybe less than 0.5 mm.

FIG. 6 shows an example performing the contrast enhanced breast imaging method according to an embodiment of the invention. Different steps S1 to S6 will be successively performed. Successive steps S1 of disposing reference film, S2 of injecting contrast agent, S3 of imaging breast, S4 of quantifying enhancement, S5 of assessing risk, will be performed.

In a step S1 of disposing reference film, a reference film is disposed on a patient breast. If a lesion has been already identified, the reference film is disposed close to that lesion. For a very first exam, with no lesion yet identified, one can proceed either without reference film or with the reference film disposed in a part of the breast where a lesion risk is less likely.

In a step S2 of injecting contrast agent, contrast agent is injected, in intravenous way, so as to propagate in the breast of the patient. Once the contrast agent has had time enough to spread within the breast veins and arteries, imaging can be performed.

Alternatively, steps S1 and S2 can be inverted.

In an option, only after the breast is compressed, the reference film containing the contrast agent is placed on top of the compression paddle in a position where the paddle is in contact with the breast.

In a step S3 of imaging breast, one or more images are taken of the breast and of the reference film simultaneously. This or these images are processed the usual way, but with a supplementary step of quantification of enhancement.

In a step S4 of quantifying enhancement, thanks to the imaged reference film zones, it will be possible to quantify the enhancement of the contrast enhanced breast image. Indeed, the reference film zones contain respectively different concentrations of contrast agent which are known concentrations. The signal intensities or signal intensity differences, which can be obtained from the contrast enhanced breast image, are also obtained for the reference film zones. Since the concentrations of contrast agent of the zones are known, a correspondence between on the one side signal intensities or signal intensity differences in the image and on the other side corresponding values of contrast agent concentration can be determined. This correspondence may take the form of a fitting function, and more particularly of a linear fitting function as shown in more detail with respect to FIG. 7.

In a step S5 of assessing risk, risk linked to detection or evolution of a lesion within the breast can be assessed. Either no lesion is already known and a new lesion in the breast can be detected, or a lesion has been already identified and its evolution can be monitored. Monitoring lesion evolution can be measuring the spreading of the original lesion throughout the breast during a sickness or regression and healing of an original lesion during a therapy. The evolution of the quantity of iodine in the lesion can also be measured.

FIG. 7 shows an example of a linear fitting function used when performing the contrast enhanced breast imaging method according to an embodiment of the invention. Other fitting functions, not linear, may be used too. In the y-axis there is the value of signal intensity SI in the contrast enhanced breast image, or a signal intensity difference in the image. In the x-axis there is the value of the contrast agent concentration C. The value of a signal intensity SI in the contrast enhanced breast image, or a signal intensity difference in the image, is plotted versus the concentration of a contrast agent C. The SI values of the three zones 71, 72 and 73, of the reference film 7, corresponding to C values of the known concentrations of the three zones 71, 72 and 73, of the reference film 7, are represented by three points P1, P2 and P3. Those three points P1, P2 and P3 are more or less aligned, since the fitting function L is indeed linear. In order to really have a linear fitting function L, with the correct slope obtained with a good precision, the three points P1, P2 and P3 should be not too close from one another and should be in the linear region of the relation between signal intensity SI and contrast agent concentration C. Therefore, the known concentrations of contrast agent are within the range 1-6 mg iodine per centimeter square for the given thickness of the reference film. The known concentrations of contrast agent are well spread all throughout this range. Besides, to get a linear fitting function with a good precision in its slope, three points are a good compromise.

The invention has been described with reference to the embodiments. However, many variations are possible within the scope of the invention.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of contrast enhanced breast imaging, comprising:
    injecting a contrast agent intravenously into a patient such that the contrast agent propagates into a breast of the patient;
    compressing the breast with a compression paddle of a breast imaging system;
    disposing a reference film insert on top of the compression paddle after the breast is compressed in a position directly above where the compression paddle is in contact with the breast, the reference film insert defining two or more zones, each zone comprising a known concentration of the contrast agent, the known concentration of the contrast agent being different for each zone;
    imaging at the same time both the breast of the patient and the reference film to obtain a global image, a portion of the global image including a contrast enhanced breast image and a portion of the global image including an image of the reference film insert; and
    quantifying contrast agent enhancement in the contrast enhanced breast image by comparing the contrast enhanced breast image and the image of the reference film insert.

2. The contrast enhanced breast imaging method according to claim 1, wherein the reference film insert has a thickness of less than 2 mm.

3. The contrast enhanced breast imaging method according to claim 2, wherein the reference film insert has a thickness of less than 1 mm.

4. The contrast enhanced breast imaging method according to claim 2, wherein the reference film insert is multi-layered with the contrast agent encapsulated in between layers.

5. The contrast enhanced breast imaging method according to claim 2, wherein the contrast agent is printed on or in the reference film insert.

6. The contrast enhanced breast imaging method according to claim 2, wherein the two or more zones comprises 3 zones.

7. The contrast enhanced breast imaging method according to claim 6, wherein the lowest concentration of the contrast agent for any of the zones is less than 2 mg iodine per centimeter square for the thickness of the reference film insert.

8. The contrast enhanced breast imaging method according to claim 7, wherein the highest concentration of the contrast agent for any of the zones is more than 5 mg iodine per centimeter square for the thickness of the reference film insert.

* * * * *